United States Patent
Kudaravalli et al.

(10) Patent No.: US 6,471,694 B1
(45) Date of Patent: Oct. 29, 2002

(54) CONTROL SYSTEM FOR CRYOSURGERY

(75) Inventors: Ravikumar V. Kudaravalli; Hong Li, both of San Diego, CA (US)

(73) Assignee: CryoGen, Inc., San Diego, CA (US)

( * ) Notice: Subject to any disclaimer, the term of this patent is extended or adjusted under 35 U.S.C. 154(b) by 0 days.

(21) Appl. No.: 09/635,108

(22) Filed: Aug. 9, 2000

(51) Int. Cl.[7] ............................................. A61B 18/18
(52) U.S. Cl. ........................................ 606/21; 606/22
(58) Field of Search ..................... 606/20–26; 62/293; 128/898

(56) References Cited

U.S. PATENT DOCUMENTS 6,007,571 A  * 12/1999 Neilson et al. ............... 606/22
6,383,180 B1 *  5/2002 Lalonde et al. ............... 606/22

* cited by examiner

Primary Examiner—Rosiland S. Kearney
(74) Attorney, Agent, or Firm—Gerald W. Spinks (57) ABSTRACT

An apparatus and method for automatic operation of a refrigeration system to provide refrigeration power to a catheter for tissue ablation or mapping. The primary refrigeration system can be open loop or closed loop, and a precool loop will typically be closed loop. Equipment and procedures are disclosed for bringing the system to the desired operational state, for controlling the operation by controlling refrigerant flow rate, for performing safety checks, and for achieving safe shutdown.

19 Claims, 8 Drawing Sheets

CONTROL SYSTEM FOR CRYOSURGERY

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention is in the field of methods and apparatus used to generate and control the delivery of cryosurgical refrigeration power to a probe or catheter.

2. Background Information

In a cryosurgical system, contaminants such as oil, moisture, and other impurities are often deposited in the impedance tubing or other restriction through which the refrigerant is pumped. In the impedance tubing, the temperature is very low, and the flow diameter is very small. Deposit of these impurities can significantly restrict the flow of the cooling medium, thereby significantly reducing the cooling power.

BRIEF SUMMARY OF THE INVENTION

A cryosurgical catheter used in a cardiac tissue ablation process should be able to achieve and maintain a low, stable, temperature. Stability is even more preferable in a catheter used in a cardiac signal mapping process. When the working pressure in a cryosurgery system is fixed, the flow rate can vary significantly when contaminants are present, thereby varying the temperature to which the probe and its surrounding tissue can be cooled. For a given cryosurgery system, there is an optimum flow rate at which the lowest temperature can be achieved, with the highest possible cooling power. Therefore, maintaining the refrigerant flow rate at substantially this optimum level is beneficial.

In either the ablation process or the mapping process, it may be beneficial to monitor the flow rates, pressures, and temperatures, to achieve and maintain the optimum flow rate. Further, these parameters can be used to more safely control the operation of the system.

A cryosurgical system which is controlled based only upon monitoring of the refrigerant pressure and catheter temperature may be less effective at maintaining the optimum flow rate, especially when contaminants are present in the refrigerant. Further, a system in which only the refrigerant pressure is monitored may not have effective safety control, such as emergency shut down control.

It may also be more difficult to obtain the necessary performance in a cryosurgery catheter in which only a single compressor is used as a refrigeration source. This is because it can be difficult to control both the low and high side pressures at the most effective levels, with any known compressor. Therefore, it can be beneficial to have separate low side and high side pressure control in a cryosurgical system.

Finally, it is beneficial to have a system for monitoring various parameters of data in a cryosurgery system over a period of time. Such parameters would include catheter temperature, high side refrigerant pressure, low side refrigerant pressure, and refrigerant flow rate. Continuous historical and instantaneous display of these parameters, and display of their average values over a selected period of time, can be very helpful to the system operator.

The present invention provides methods and apparatus for controlling the operation of a cryosurical catheter refrigeration system by monitoring pressures, temperature, and/or flow rate, in order to automatically maintain a stable refrigerant flow rate at or near an optimum level for the performance of crysurgical tissue ablation or mapping. Different refrigerant flow rates can be selected as desired for ablation or mapping. Flow rate, pressures, and temperature can be used for automatic shut down control. Refrigerant sources which provide separate high side and low side pressure controls add to the performance of the system. Continuous displays of temperature, high side refrigerant pressure, low side refrigerant pressure, and refrigerant flow rate are provided to the operator on a single display, to enhance system efficiency and safety.

The novel features of this invention, as well as the invention itself, will be best understood from the attached drawings, taken along with the following description, in which similar reference characters refer to similar parts, and in which:

DETAILED DESCRIPTION OF THE INVENTION

According to certain embodiments of the invention, the refrigeration system may be a two stage Joule-Thomson system with a closed loop precool circuit and either an open loop or a closed loop primary circuit. A typical refrigerant for the primary circuit would be R-508b, and a typical refrigerant for the precool circuit would be R-410a. In the ablation mode, the system may be capable of performing tissue ablation at or below minus 70° C. while in contact with the tissue and circulating blood. In the mapping mode, the system may be capable of mapping by stunning the tissue at a temperature between minus 10° C. and minus 18° C. while in contact with the tissue and circulating blood. These performance levels may be achieved while maintaining the catheter tip pressure at or below a sub-diastolic pressure of 14 psia.

Figure 1:
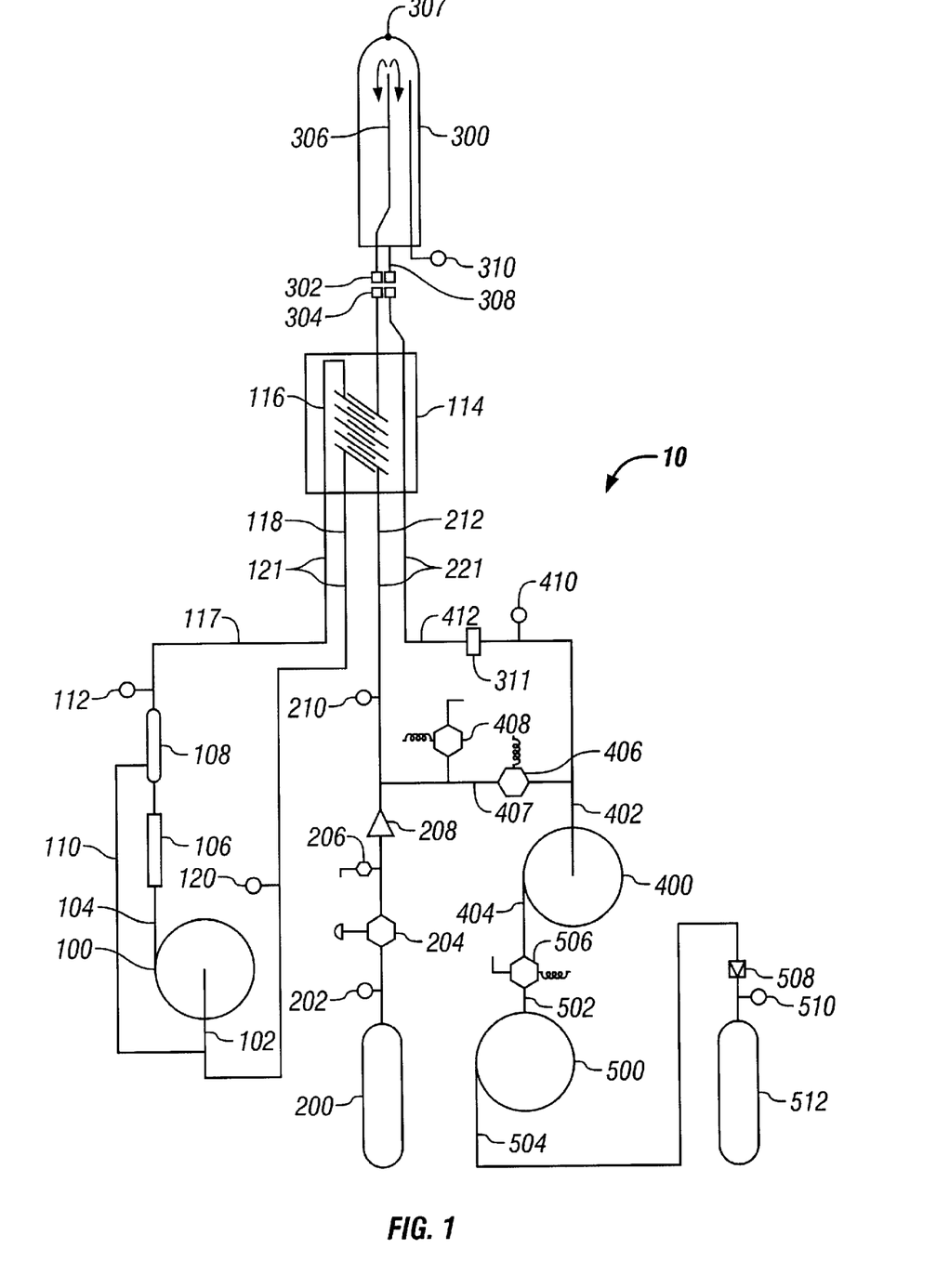
FIG. 1 is a schematic of a first embodiment of the apparatus of the present invention, using a pressure bottle as the primary refrigerant source.

As shown in FIG. 1, one embodiment of the apparatus 10 of the present invention is an open loop system using a pressure bottle for the refrigerant source. Such a system can include a primary refrigerant supply bottle 200, a primary refrigerant fluid controller 208, a catheter 300, a primary refrigerant recovery bottle 512, a secondary refrigerant compressor 100, a precool heat exchanger 114, and various sensors. In certain embodiments, all but the catheter 300 and the precool heat exchanger 114 may be located in a cooling console housing. The precool heat exchanger 114 is connected to the console by flexible lines 121, 221. Pressure of the refrigerant in the primary refrigerant supply bottle 200 is monitored by a primary refrigerant supply pressure sensor 202. Output of primary refrigerant from the supply bottle 200 is regulated by a pressure regulator 204, which, in certain embodiments, can receive refrigerant from the bottle 200 at a pressure above 350 psia and regulate it to less than 350 psia. A primary refrigerant relief valve 206 is provided to prevent over pressurization of the primary system downstream of the pressure regulator 204, for example, above 400 psia. The flow rate of primary refrigerant is controlled by the fluid controller 208, which can be either a pressure controller or a flow controller. A feedback loop may be provided to control the operation of the fluid controller 208. The feedback signal for the fluid controller 208 can come from a pressure sensor 310 or a flow sensor 311, on the effluent side of the catheter 300, discussed below.

A primary refrigerant high pressure sensor 210 is provided downstream of the fluid controller 208, to monitor the primary refrigerant pressure applied to the precool heat exchanger 114. The high pressure side 212 of the primary loop passes through the primary side of the cooling coil of the precool heat exchanger 114, then connects to a quick connect fitting 304 on the precool heat exchanger 114. Similarly, the low side quick connect fitting 304 on the precool heat exchanger 114 is connected to the low pressure side 412 of the primary loop, which passes back through the housing of the precool heat exchanger 114, without passing through the cooling coil, and then through the flow sensor 311. The catheter tip pressure sensor 310 monitors catheter effluent pressure in the tip of the catheter 300. The control system maintains catheter tip pressure at a sub-diastolic level at all times.

The low pressure side 412 of the primary loop can be connected to the inlet 402 of a vacuum pump 400. A primary refrigerant low pressure sensor 410 monitors pressure in the low side 412 of the primary loop downstream of the precool heat exchanger 114. The outlet 404 of the vacuum pump 400 can be connected to the inlet 502 of a recovery pump 500. A 3 way, solenoid operated, recovery valve 506 is located between the vacuum pump 400 and the recovery pump 500. The outlet 504 of the recovery pump 500 is connected to the primary refrigerant recovery bottle 512 via a check valve 508. A primary refrigerant recovery pressure sensor 510 monitors the pressure in the recovery bottle 512. A 2 way, solenoid operated, bypass valve 406 is located in a bypass loop 407 between the low side 412 of the primary loop upstream of the vacuum pump 400 and the high side 212 of the primary loop downstream of the fluid controller 208. A solenoid operated bypass loop vent valve 408 is connected to the bypass loop 407.

In the catheter 300, the high pressure primary refrigerant flows through an impedance device such as a capillary tube 306, then expands into the distal portion of the catheter 300, where the resultant cooling is applied to surrounding tissues. A catheter tip temperature sensor 307, such as a thermocouple, monitors the temperature of the distal portion of the catheter 300. A catheter return line 308 returns the effluent refrigerant from the catheter 300 to the precool heat exchanger 114. The high and low pressure sides of the catheter 300 are connected to the heat exchanger quick connects 304 by a pair of catheter quick connects 302. As an alternative to pairs of quick connects 302, 304, coaxial quick connects can be used. In either case, the quick connects may carry both refrigerant flow and electrical signals.

In the precool loop, compressed secondary refrigerant is supplied by a precool compressor 100. An after cooler 106 can be connected to the outlet 104 of the precool compressor 100 to cool and condense the secondary refrigerant. An oil separator 108 can be connected in the high side 117 of the precool loop, with an oil return line 110 returning oil to the precool compressor 100. A high pressure precooler pressure sensor 112 senses pressure in the high side 117 of the precool loop. The high side 117 of the precool loop is connected to an impedance device such as a capillary tube 116 within the housing of the precool heat exchanger 114. High pressure secondary refrigerant flows through the capillary tube 116, then expands into the secondary side of the cooling coil of the precool heat exchanger 114, where it cools the high pressure primary refrigerant. The effluent of the secondary side of the precool heat exchanger 114 returns via the low side 118 of the precool loop to the inlet 102 of the precool compressor 100. A low pressure precooler pressure sensor 120 senses pressure in the low side 118 of the precool loop.

Figure 2:
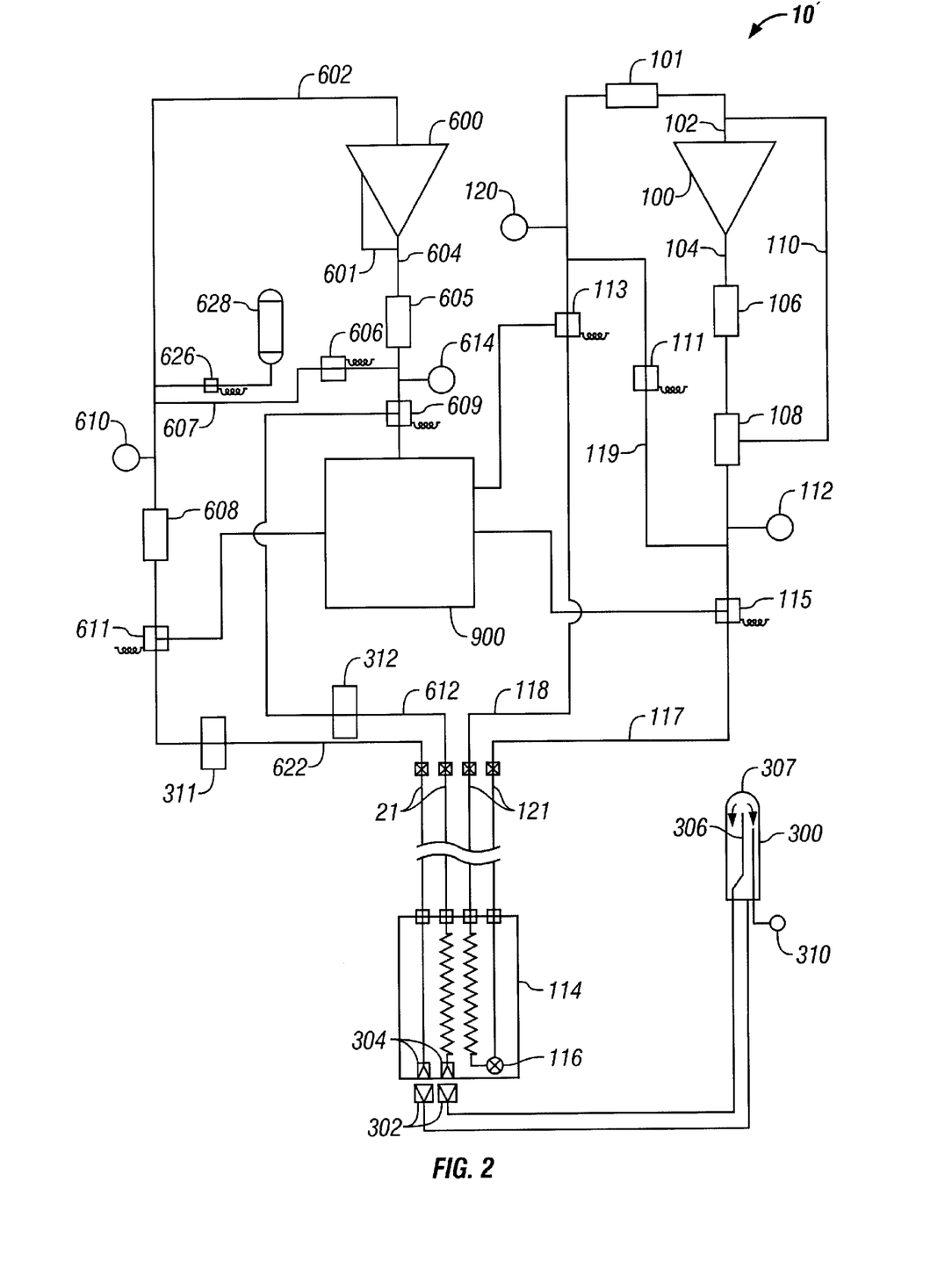
FIG. 2 is a schematic of a second embodiment of the apparatus of the present invention, using a compressor as the primary refrigerant source.

Instead of using primary refrigerant supply and return bottles, the apparatus can use one or more. primary compressors in a closed loop system. FIG. 2 shows a second embodiment of the apparatus of the present invention, with a single compressor system. This embodiment would be appropriate in applications where the high side and low side pressures can be adequately controlled with a single compressor. In the apparatus 10' of this type of system, the low side 622 of the primary loop conducts the effluent of the catheter 300 to the inlet 602 of a primary refrigerant compressor 600. The compressor 600 compresses the primary refrigerant, and returns it from the compressor outlet 604 via the high side 612 of the primary loop to the primary side of the precool heat exchanger 114. A primary refrigerant high pressure sensor 614 is provided in the high side 612 of the primary loop, to monitor the primary refrigerant pressure applied to the precool heat exchanger 114. A primary refrigerant high pressure flow sensor 312 can be provided in the high side 612 of the primary loop. A primary refrigerant low pressure sensor 610 monitors pressure in the low side 622 of the primary loop downstream of the precool heat exchanger 114. A primary loop filter 608 can be provided in the low side 622 of the primary loop. A 2way, solenoid operated, primary refrigerant charge valve 626 and a primary refrigerant reservoir 628 can be provided in the low side 622 of the primary loop. A high pressure after-cooler 605 can be provided downstream of the primary refrigerant compressor 600.

As further shown in FIG. 2, a 2 way, solenoid operated, primary loop bypass valve 606 is located in a bypass loop 607 between the low side 622 of the primary loop upstream of the compressor 600 and the high side 612 of the primary loop downstream of the compressor 600. Opening of the primary loop bypass valve 606 can facilitate startup of the primary compressor 600. A precool loop filter 101 can be provided in the low side 118 of the precool loop. Further, a 2 way, solenoid operated, precool loop bypass valve 111 is located in a bypass loop 119 between the low side 118 of the precool loop upstream of the compressor 100 and the high side 117 of the precool loop downstream of the compressor 100. Opening of the precool loop bypass valve 111 can facilitate startup of the precool compressor 100.

A purification system 900 can be provided for removing contaminants from the primary refrigerant and the secondary refrigerant. Solenoid operated 3 way purification valves 609, 611 are provided in the high side and low side, respectively, of the primary loop, for selectively directing the primary refrigerant through the purification system 900. Similarly, solenoid operated 3 way purification valves 115, 113 are provided in the high side and low side, respectively, of the precool loop, for selectively directing the secondary refrigerant through the purification system 900.

The remainder of the precool loop, the precool heat exchanger 114, and the catheter 300 are the same as discussed above for the first embodiment.

Figure 3:
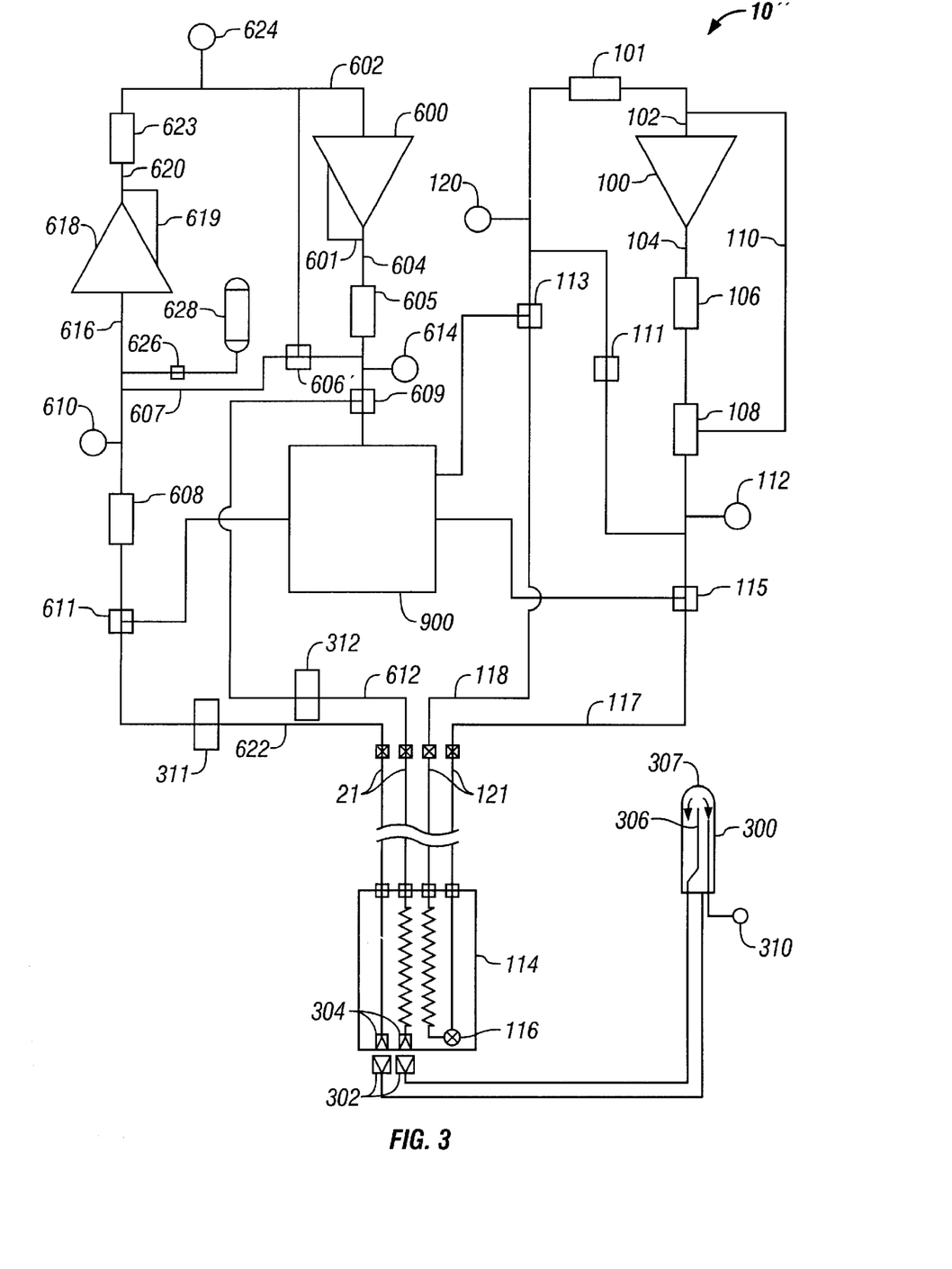
FIG. 3 is a schematic of a third embodiment of the apparatus of the present invention, using two compressors connected in series as the primary refrigerant source.

In applications where separate low side and high side pressure control is required, but where a closed loop system is desired, a two compressor primary system may be used. FIG. 3 shows a third embodiment of the apparatus of the present invention, with a dual compressor system. In the apparatus 10" of this type of system, the low side 622 of the primary loop conducts the effluent of the catheter 300 to the inlet 616 of a low side primary refrigerant compressor 618. The low side compressor 618 compresses the primary refrigerant, and provides it via its outlet 620 to the inlet 602 of a high side primary refrigerant compressor 600. A low pressure after-cooler 623 can be provided downstream of the low side compressor 618. The high side compressor 600 further compresses the primary refrigerant to a higher pressure and returns it via its outlet 604 and via the high side 612 of the primary loop to the primary side of the precool heat exchanger 114. A primary refrigerant high pressure sensor 614 is provided in the high side 612 of the primary loop, to monitor the high side primary refrigerant pressure upstream of the precool heat exchanger 114. A primary refrigerant low pressure sensor 610 monitors pressure in the low side 622 of the primary loop downstream of the precool heat exchanger 114. A primary refrigerant intermediate pressure sensor 624 monitors pressure between the outlet 620 of the low side compressor 618 and the inlet 602 of the high side compressor 600. The high side compressor 600 and the low side compressor 618 are separately controlled, using feedback from the catheter tip pressure sensor 310 and/or the flow sensors 311, 312.

As further shown in FIG. 3, a 3 way, solenoid operated, bypass valve 606' is located in a bypass loop 607 between the low side 622 of the primary loop upstream of the low side compressor 618 and the high side 612 of the primary loop downstream of the high side compressor 600. A third port is connected between the high side and low side compressors. The precool loop, the precool heat exchanger 114, and the catheter 300 are the same as discussed above for the first and second embodiments.

Figure 4:
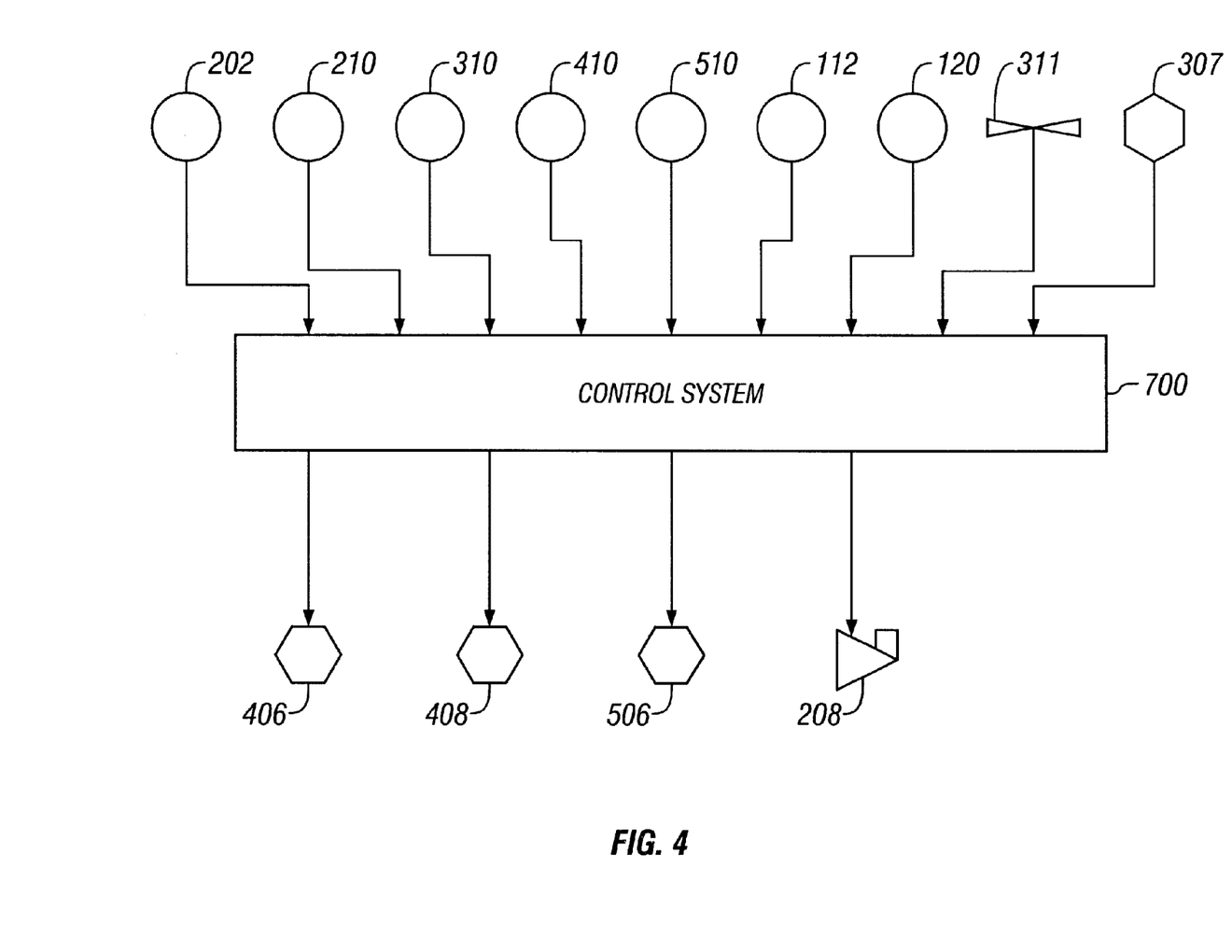
FIG. 4 is a schematic of a first embodiment of a control system apparatus according to the present invention, for use with the apparatus shown in FIG. 1.

FIG. 4 shows a control diagram which would be suitable for use with the apparatus shown in FIG. 1. A computerized automatic control system 700 is connected to the various sensors and control devices to sense and control the operation of the system, and to provide safety measures, such as shut down schemes. More specifically, on the sensing side, the low pressure precool sensor 120 inputs low side precool pressure PA, the high pressure precool sensor 112 inputs high side precool pressure PB, the primary supply pressure sensor 202 inputs supply bottle pressure P1, the primary recovery pressure sensor 510 inputs recovery bottle pressure P2, the high pressure primary sensor 210 inputs high side primary pressure P3, the low pressure primary sensor 410 inputs low side primary pressure P4, the catheter tip pressure sensor 310 inputs catheter tip pressure P5, the temperature sensor 307 inputs catheter tip temperature T, and the flow sensor 311 inputs primary refrigerant flow rate F. Further, on the control side, the control system 700 energizes the normally closed bypass valve 406 to open it, energizes the normally open vent valve 408 to close it, and energizes the recovery valve 506 to connect the vacuum pump outlet 404 to the recovery pump inlet 502. Finally, the control system 700 provides a pressure set point SPP or flow rate set point SPF to the fluid controller 208, depending upon whether it is a pressure controller or a flow controller.

Figure 5:
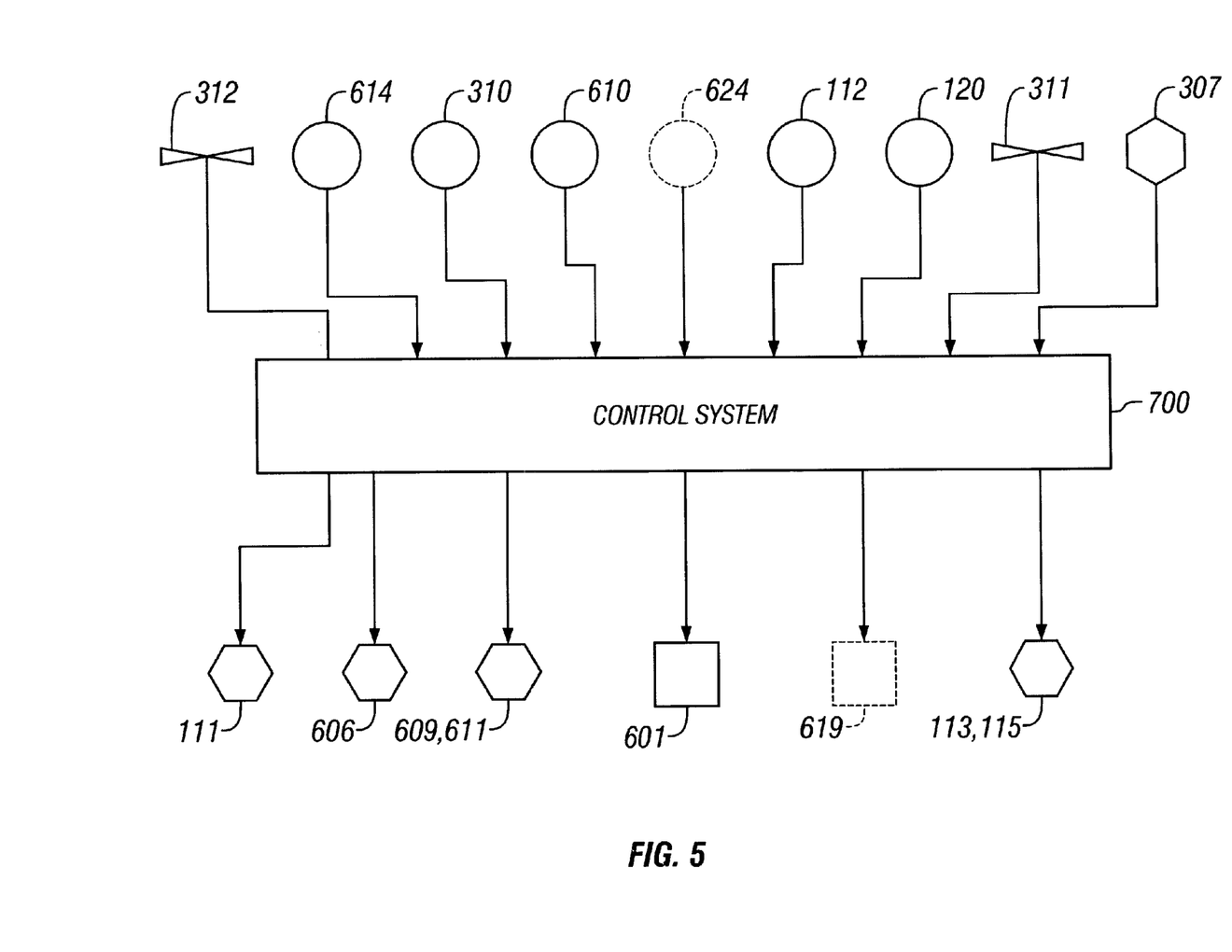
FIG. 5 is a schematic of a second embodiment of a control system apparatus according to the present invention, for use with the apparatus shown in FIG. 2 or 3.

FIG. 5 shows a control diagram which would be suitable for use with the apparatus shown in FIG. 2 or FIG. 3. A computerized automatic control system 700 is connected to the various sensors and control devices to sense and control the operation of the system, and to provide safety measures, such as shut down schemes. More specifically, on the sensing side, the low pressure precool sensor 120 inputs low side precool pressure PA, the high pressure precool sensor 112 inputs high side precool pressure PB, the high pressure primary sensor 614 inputs high side primary pressure P3, the low pressure primary sensor 610 inputs low side primary pressure P4, the catheter tip pressure sensor 310 inputs catheter tip pressure P5, the temperature sensor 307 inputs catheter tip temperature T, and the flow sensors 311, 312 input primary refrigerant flow rate F. Further, on the control side, the control system 700 energizes the normally closed primary loop bypass valve 606, 606' to open it, and the control system 700 energizes the normally closed precool loop bypass valve 111 to open it. The control system 700 also energizes the primary loop purification valves 609, 611 to selectively purify the primary refrigerant, and the control system 700 energizes the precool loop purification valves 113, 115 to selectively purify the secondary refrigerant. Finally, the control system 700 provides a minimum high side pressure set point PL2 to the controller 601 of the primary compressor 600 in the system shown in FIG. 2. Alternatively, in the system shown in FIG. 3, the control system 700 provides a minimum high side pressure set point PL2B to the controller 601 of the high side primary compressor 600, and the control system 700 provides a maximum low side pressure set point PL2A to the controller 619 of the low side primary compressor 618.

Figure 6:
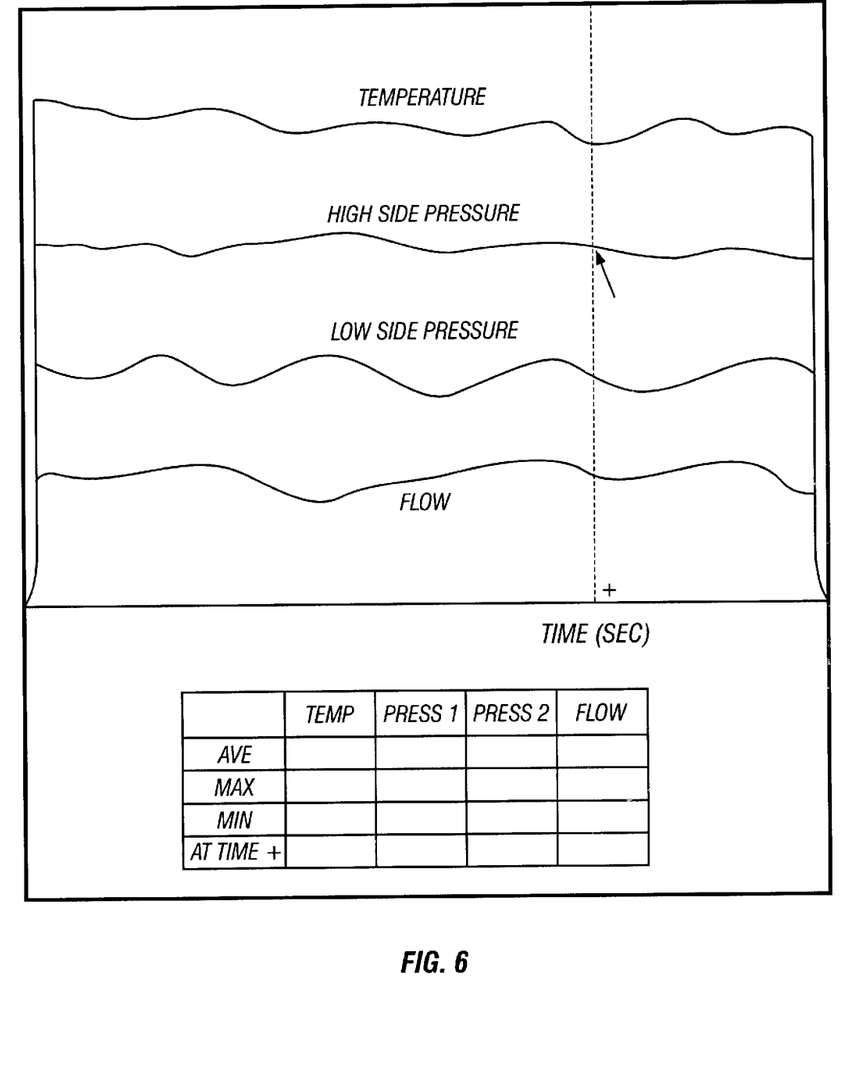
FIG. 6 is a schematic of a parameter display for use with the control equipment of the present invention.

A numeric digital display, or a graphical display similar to that shown in FIG. 6, is provided on the cooling console to assist the operator in monitoring and operating the system. For example, on a single graphical display, graphs can be shown of catheter tip temperature T, high side primary pressure P3, low side primary pressure P4, and primary flow rate F, all versus time. Further, on the same display, the operator can position a vertical cursor at a selected time, resulting in the tabular display of the instantaneous values of T, P3, P4, and F, as well as the average, maximum, and minimum values of these parameters.

The present invention will now be further illustrated by describing a typical operational sequence of the open loop embodiment, showing how the control system 700 operates the remainder of the components to start up the system, to provide the desired refrigeration power, and to provide system safety. The system can be operated in the Mapping Mode, where the cold tip temperature might be maintained at minus 10 C., or in the Ablation Mode, where the cold tip temperature might be maintained at minus 65 C. Paragraphs are keyed to the corresponding blocks in the flow diagram shown in FIG. 7. Suggested exemplary Pressure Limits used below could be PL1=160 psia; PL2=400 psia; PL3=500 psia; PL4=700 psia; PL5=600 psia; PL6=5 psia; PL7= diastolic pressure; PL8=375 psia; and PL9=5 psia. Temperature limits, flow limits, procedure times, and procedure types are set by the operator according to the procedure being performed.

Figure 7A:
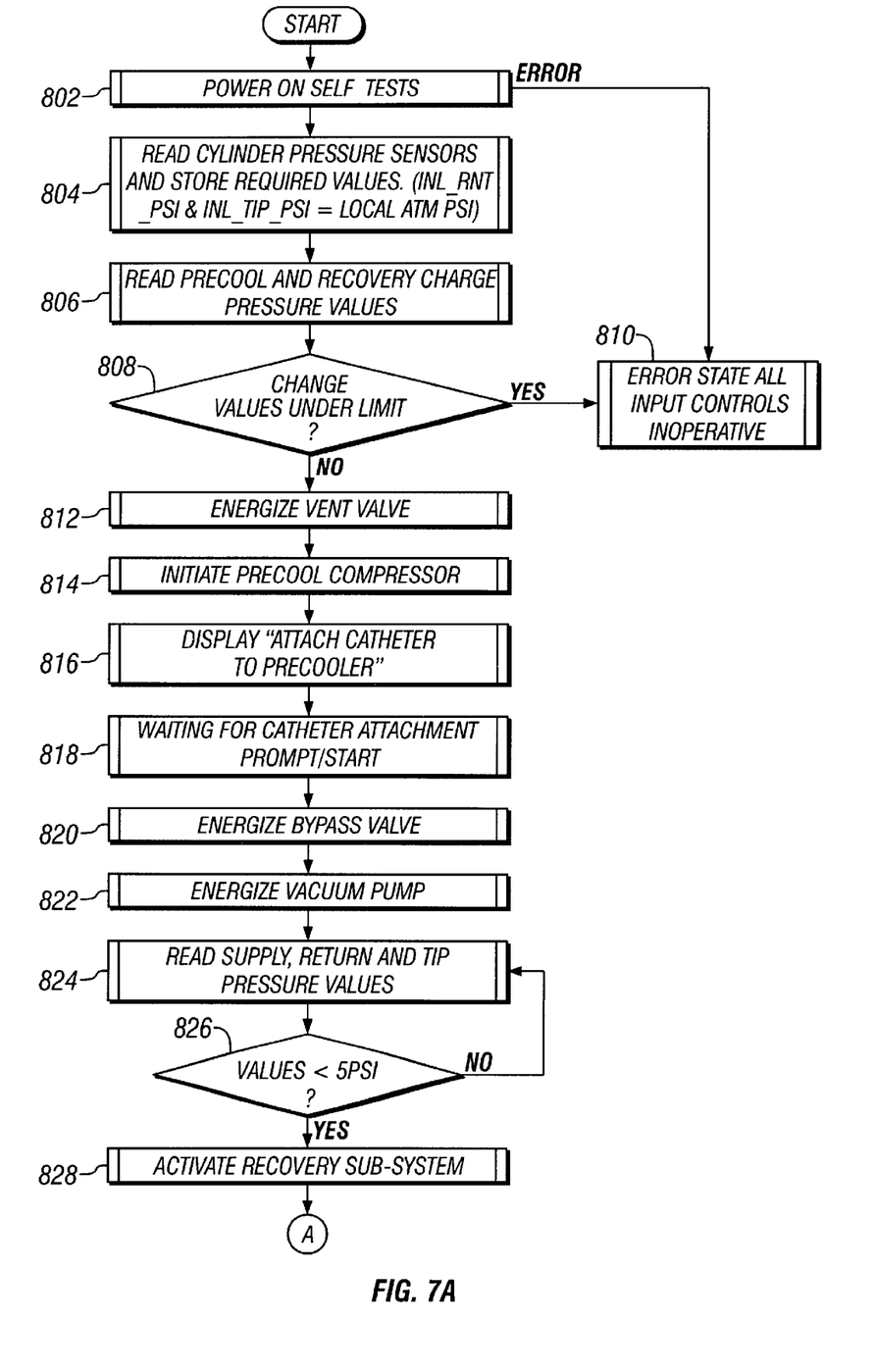
FIG. 7 is a flow diagram showing one control sequence for use with the control apparatus of the present invention.
Figure 7B:
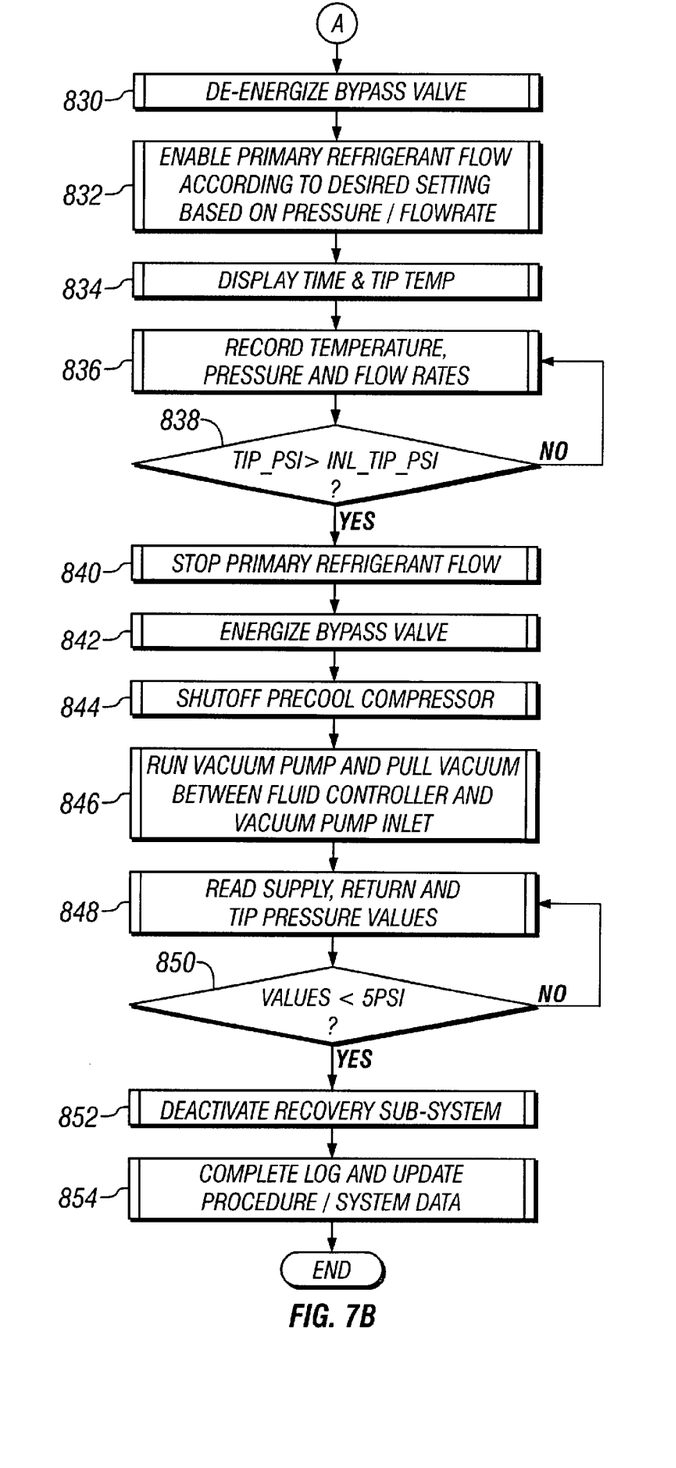

Perform self tests (block 802) of the control system circuitry and connecting circuitry to the sensors and controllers to insure circuit integrity.

Read and store supply cylinder pressure P1, primary low pressure P4, and catheter tip pressure P5 (block 804). At this time, P4 and P5 are at atmospheric pressure. If P1 is less than Pressure Limit PL2 (block 808), display a message to replace the supply cylinder (block 810), and prevent further operation. If P1 is greater than PL2, but less than Pressure Limit PL3, display a message to replace the supply cylinder soon, but allow operation to continue.

Read precool charge pressure PB and recovery cylinder pressure P2 (block 806). If PB is less than Pressure Limit PL1 (block 808), display a message to service the precool loop (block 810), and prevent further operation. If P2 is greater than Pressure Limit PL4 (block 808), display a message to replace the recovery cylinder (block 810), and prevent further operation. If P2 is less than PL4, but greater than Pressure Limit PL5, display a message to replace the recovery cylinder soon, but allow operation to continue.

Energize the bypass loop vent valve 408 (block 812). The vent valve 408 is a normally open two way solenoid valve open to the atmosphere. When energized, the vent valve 408 is closed.

Start the precool compressor 100 (block 814). Display a message to attach the catheter 300 to the console quick connects 304 (block 816). Wait for the physician to attach the catheter 300, press either the Ablation Mode key or the Mapping Mode key, and press the Start key (block 818). Read the catheter tip temperature T and the catheter tip pressure P5. At this time, T is the patient's body temperature and P5 is atmospheric pressure.

Energize the bypass loop valve 406, while leaving the recovery valve 506 deenergized (block 820). The bypass valve 406 is a normally closed 2 way solenoid valve. Energizing the bypass valve 406 opens the bypass loop. The recovery valve 506 is a three way solenoid valve that, when not energized, opens the outlet of the vacuum pump 400 to atmosphere. Start the vacuum pump 400 (block 822). These actions will pull a vacuum in the piping between the outlet of the fluid controller 208 and the inlet of the vacuum pump 400, including the high and low pressure sides of the catheter 300. Monitor P3, P4, and P5 (block 824), until all three are less than Pressure Limit PL6 (block 826).

Energize the recovery valve 506 and the recovery pump 500 (block 828). When energized, the recovery valve 506 connects the outlet of the vacuum pump 400 to the inlet of the recovery pump 500. De-energize the bypass valve 406, allowing it to close (block 830). Send either a pressure set point SPP (if a pressure controller is used) or a flow rate set point SPF (if a flow controller is used) to the fluid controller 208 (block 832). Where a pressure controller is used, the pressure set point SPP is at a pressure which will achieve the desired refrigerant flow rate, in the absence of plugs or leaks. The value of the set point is determined according to whether the physician has selected the mapping mode or the ablation mode. These actions start the flow of primary refrigerant through the catheter 300 and maintain the refrigerant flow rate at the desired level.

Continuously monitor and display procedure time and catheter tip temperature T (block 834). Continuously monitor and display all pressures and flow rates F (block 836). If catheter tip pressure P5 exceeds Pressure Limit PL7, start the shutdown sequence (block 840). Pressure Limit PL7 is a pressure above which the low pressure side of the catheter 300 is not considered safe.

If F falls below Flow Limit FL1, and catheter tip temperature T is less than Temperature Limit TL1, start the shutdown sequence (block 840). Flow Limit FL1 is a minimum flow rate below which it is determined that a leak or a plug has occurred in the catheter 300. FL1 can be expressed as a percentage of the flow rate set point SPF. Temperature Limit TL1 is a temperature limit factored into this decision step to prevent premature shutdowns before the catheter 300 reaches a steady state at the designed level of refrigeration power. So, if catheter tip temperature T has not yet gone below TL1, a low flow rate will not cause a shutdown.

If P3 exceeds Pressure Limit PL8, and F is less than Flow Limit FL2, start the shutdown sequence (block 840). PL8 is a maximum safe pressure for the high side of the primary system. Flow Limit FL2 is a minimum flow rate below which it is determined that a plug has occurred in the catheter 300, when PL8 is exceeded. FL2 can be expressed as a percentage of the flow rate set point SPF.

If P4 is less than Pressure Limit PL9, and F is less than Flow Limit FL3, start the shutdown sequence (block 840). PL9 is a pressure below which it is determined that a plug has occurred in the catheter 300, when flow is below FL3. FL3 can be expressed as a percentage of the flow rate set point SPF.

An exemplary shutdown sequence will now be described. Send a signal to the fluid controller 208 to stop the primary refrigerant flow (block 840). Energize the bypass valve 406 to open the bypass loop (block 842). Shut off the precool compressor 100 (block 844). Continue running the vacuum pump 400 to pull a vacuum between the outlet of the fluid controller 208 and the inlet of the vacuum pump 400 (block 846). Monitor primary high side pressure P3, primary low side pressure P4, and catheter tip pressure P5 (block 848) until all three are less than the original primary low side pressure which was read in block 804 at the beginning of the procedure (block 850). Then, de-energize the recovery pump 500, recovery valve 506, vent valve 408, bypass valve 406, and vacuum pump 400 (block 852). Display a message suggesting the removal of the catheter 300, and update a log of all system data (block 854).

Similar operational procedures, safety checks, and shutdown procedures would be used for the closed loop primary system shown in FIG. 2 or FIG. 3, except that the primary compressor 600 or compressors 600, 618 would provide the necessary primary refrigerant flow rate in place of the supply and recovery cylinders, the fluid controller, and the vacuum and recovery pumps. As with the open loop system, the closed loop system can be operated in the Mapping Mode, where the cold tip temperature might be maintained at minus 10 C., or in the Ablation Mode, where the cold tip temperature might be maintained at minus 65 C. As a first option to achieve the desired cold tip temperature, the precool bypass valve 111 can be adjusted to control the liquid fraction resulting after expansion of the secondary refrigerant, thereby adjusting the refrigeration capacity. Under this option, primary refrigerant high and low pressures are kept constant. As a second option, or in combination with the first option, primary refrigerant flow rate can be by means of operating controllers 601, 619 on the primary compressors 600, 618 to maintain a high pressure set point SPP which will achieve the desired flow rate, resulting in the desired cold tip temperature.

A Service Mode is possible, for purification of the primary and secondary refrigerants. In the Service Mode, the normally open bypass valves 111, 606 are energized to close.

The primary loop purification valves 609, 611 are selectively aligned with the purification system 900 to purify the primary refrigerant, or the precool loop purification valves 113, 115 are selectively aligned with the purification system 900 to purify the secondary refrigerant.

In either the Mapping Mode or the Ablation Mode, the desired cold tip temperature control option is input into the control system 700. Further, the type of catheter is input into the control system 700. The normally closed charge valve 626 is energized as necessary to build up the primary loop charge pressure. If excessive charging is required, the operator is advised. Further, if precool loop charge pressure is below a desired level, the operator is advised.

When shutdown is required, the primary loop high side purification valve 609 is closed, and the primary loop compressors 600, 618 continue to run, to draw a vacuum in the catheter 300. When the desired vacuum is achieved, the primary loop low side purification valve 611 is closed. This isolates the primary loop from the catheter 300, and the disposable catheter 300 can be removed.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. Apparatus for performing cryosurgery, comprising:
   a refrigerant supply source connectable to a high pressure duct;
   a cryosurgery catheter having an inlet connectable to said high pressure duct, said catheter having a tip;
   a refrigerant expansion element in said catheter;
   a temperature sensor on said catheter;
   a pressure sensor adapted to sense pressure inside said catheter tip;
   a low pressure duct connectable to an outlet of said catheter;
   a flow sensor in said low pressure duct downstream of said catheter; and
   a control system connected and programmed to maintain a selected catheter temperature, in response to signals from said temperature sensor, said pressure sensor, and said flow sensor.

2. An apparatus as recited in claim 1, further comprising:
   a precool heat exchanger in said high pressure duct;
   a precool compressor for compressing a secondary refrigerant; and
   a precool expansion element connected to said precool compressor for expanding said secondary refrigerant to cool said precool heat exchanger.

3. An apparatus as recited in claim 2, further comprising a bypass valve connected between an outlet of said precool compressor and an inlet of said precool compressor.

4. An apparatus as recited in claim 1, wherein:
   said refrigerant supply source comprises a pressure bottle; and
   a fluid controller in said high pressure duct; and
   further comprising a recovery bottle connected to said low pressure duct.

5. An apparatus as recited in claim 4, wherein said fluid controller comprises a pressure controller.

6. An apparatus as recited in claim 4, wherein said fluid controller comprises a flow controller.

7. An apparatus as recited in claim 4, further comprising:
   a vacuum pump having an inlet connected to said low pressure duct;
   a recovery pump having an inlet connected to an outlet of said vacuum pump, said recovery pump having an outlet connected to said recovery bottle;
   a bypass valve in a bypass duct connected between said high pressure duct and said low pressure duct; and
   a vent valve connected to said bypass duct between said bypass valve and said high pressure duct.

8. An apparatus as recited in claim 1, wherein:
   said refrigerant supply source comprises a compressor;
   said high pressure duct is connected to an outlet of said compressor;
   a compressor controller; and
   said control system operates said compressor controller to maintain refrigerant pressure above a selected level in said high pressure duct.

9. An apparatus as recited in claim 8, further comprising a second compressor with a second compressor controller; wherein:
   said low pressure duct is connected to an inlet of said second compressor;
   an outlet of said second compressor is connected to an inlet of said first compressor;
   said control system operates said first compressor controller to maintain refrigerant pressure above a selected level in said high pressure duct; and
   said control system operates said second compressor controller to maintain refrigerant pressure below a selected level in said low pressure duct.

10. An apparatus as recited in claim 8, further comprising a bypass valve in a bypass duct connected between said high pressure duct and said low pressure duct.

11. An apparatus as recited in claim 1, further comprising:
    a precool heat exchanger in said high pressure duct;
    a precool compressor for compressing a secondary refrigerant;
    a precool expansion element connected to said precool compressor for expanding said secondary refrigerant to cool said precool heat exchanger; and
    a bypass valve connected between an outlet of said precool compressor and an inlet of said precool compressor
    wherein:
    said refrigerant supply source comprises a primary compressor;
    said high pressure duct is connected to an outlet of said primary compressor; and
    said control system operates said bypass valve to maintain catheter temperature at a selected level.

12. Apparatus for performing cryosurgery, comprising:
    a primary refrigerant pressure bottle connectable to a high pressure duct;
    a fluid pressure controller in said high pressure duct;
    a precool heat exchanger in said high pressure duct;
    a precool compressor for compressing a secondary refrigerant;
    a secondary expansion element connected to expand said secondary refrigerant to cool said precool heat exchanger;
    a cryosurgery catheter having an inlet connectable to said high pressure duct;

a primary expansion element in said catheter connected to expand said primary refrigerant to cool a portion of said catheter;

a temperature sensor on said catheter;

a low pressure duct connectable to an outlet of said catheter;

a pressure sensor in said low pressure duct;

a flow sensor in said low pressure duct;

a vacuum pump having an inlet connected to said low pressure duct;

a recovery pump having an inlet connected to an outlet of said vacuum pump;

a recovery bottle connected to an outlet of said recovery pump;

a bypass valve in a bypass duct connected between said high pressure duct and said low pressure duct; and a control system connected and programmed to operate said pressure controller to maintain a selected primary refrigerant flow rate, in response to signals from said temperature sensor, said pressure sensor, and said flow sensor.

13. A method for controlling a cryosurgical instrument, comprising:

providing a refrigerant supply, a cryosurgery catheter including an expansion element, a temperature sensor, a pressure sensor, a flow sensor, a precool loop, and a control system connected to said sensors;

flowing said refrigerant via a high pressure duct into said cryosurgery catheter;

precooling said refrigerant in said precool loop;

expanding said refrigerant in said catheter with said expansion element;

sensing the temperature of said catheter with said temperature sensor;

sensing the pressure of said expanded refrigerant with said pressure sensor;

sensing the flow rate of said refrigerant with said flow sensor; and controlling said refrigerant with said control system, to maintain a selected catheter temperature, in response to signals from said temperature sensor, said pressure sensor, and said flow sensor.

14. A method as recited in claim 13, wherein:

said refrigerant supply source comprises a pressure bottle; and a fluid controller in said high pressure duct;

said method comprising operating said fluid controller to maintain a selected pressure at said pressure sensor.

15. A method as recited in claim 14, wherein said fluid controller comprises a pressure controller, said method comprising modifying a pressure setpoint of said pressure controller to maintain a selected pressure at said pressure sensor.

16. A method as recited in claim 14, wherein said fluid controller comprises a flow controller, said method comprising modifying a flow setpoint of said flow controller to maintain a selected pressure at said pressure sensor.

17. A method as recited in claim 13, wherein:

said refrigerant supply source comprises a compressor; and a compressor controller;

said method comprising operating said compressor controller to maintain a selected pressure at said pressure sensor.

18. A method as recited in claim 17, further comprising:

providing a second compressor with a second compressor controller, wherein a low pressure duct is connected between said catheter and an inlet of said second compressor, and an outlet of said second compressor is connected to an inlet of said first compressor;

operating said control system and said first controller to maintain refrigerant pressure above a selected level in said high pressure duct; and operating said control system and said second controller to maintain refrigerant pressure below a selected level in said low pressure duct.

19. A method as recited in claim 13, wherein:

said refrigerant supply source comprises a compressor; and a precool bypass valve in said precool loop;

said method comprising operating said precool bypass valve to maintain a selected catheter temperature.

* * * * *